United States Patent
Ujihara et al.

(10) Patent No.: US 10,386,314 B2
(45) Date of Patent: Aug. 20, 2019

(54) APPARATUS AND METHOD FOR MEASURING ENERGY OF ELECTRONS

(71) Applicant: NATIONAL UNIVERSITY CORPORATION NAGOYA UNIVERSITY, Nagoya-shi, Aichi (JP)

(72) Inventors: Toru Ujihara, Nagoya (JP); Fumiaki Ichihashi, Nagoya (JP); Takahiko Kawaguchi, Nagoya (JP); Takahiro Ito, Nagoya (JP); Makoto Kuwahara, Nagoya (JP); Peter Baltzer, Uppsala (SE); Yukio Takeuchi, Nishitama-gun (JP)

(73) Assignee: NATIONAL UNIVERSITY CORPORATION NAGOYA UNIVERSITY, Nagoya-shi (JP)

(*) Notice: Subject to any disclaimer, the term of this patent is extended or adjusted under 35 U.S.C. 154(b) by 0 days.

(21) Appl. No.: 15/772,501
(22) PCT Filed: Nov. 2, 2016
(86) PCT No.: PCT/JP2016/082700
§ 371 (c)(1),
(2) Date: Apr. 30, 2018
(87) PCT Pub. No.: WO2017/078111
PCT Pub. Date: May 11, 2017

(65) Prior Publication Data
US 2019/0079033 A1    Mar. 14, 2019

(30) Foreign Application Priority Data
Nov. 2, 2015 (JP) .................. 2015-215784

(51) Int. Cl.
*G01N 23/227* (2018.01)
*H01J 49/48* (2006.01)
(Continued)

(52) U.S. Cl.
CPC .......... *G01N 23/2273* (2013.01); *H01J 49/46* (2013.01); *G01N 2223/085* (2013.01)

(58) Field of Classification Search
CPC .......... G01N 23/2273; G01N 2223/085; H01J 49/46
(Continued)

(56) References Cited

U.S. PATENT DOCUMENTS

| 2010/0108882 A1* | 5/2010 | Zewail | H01J 37/22 250/307 |
| 2015/0206732 A1* | 7/2015 | Sakai | G01N 23/02 378/64 |

(Continued)

FOREIGN PATENT DOCUMENTS

| JP | S51-045586 A | 4/1976 |
| JP | S61-264241 A | 11/1986 |

(Continued)

OTHER PUBLICATIONS

Jan. 24, 2017 International Search Report issued in Patent Application No. PCT/JP2016/082700.
(Continued)

*Primary Examiner* — Nicole M Ippolito
(74) *Attorney, Agent, or Firm* — Oliff PLC

(57) ABSTRACT

Electrons excited by irradiation of a visible light to a sample is at an energy level lower than a vacuum level, thus photoelectrons are not emitted from the sample and energy of excited electrons cannot be measured. The visible light is irradiated to the sample through a mesh electrode. A surface film for reducing the vacuum level is formed on a surface of the sample. With the surface film being formed, photoelectrons are obtained by the visible light, and these photoelectrons are accelerated by the mesh electrode toward a photoelectron spectrometer. Ultraviolet light may be irradiated to the sample and metal having same potential therewith. In this case, the mesh electrode is set at a retracted position to prohibit interaction of the mesh electrode and the ultraviolet
(Continued)

light. A difference between the valence band and the Fermi level of the sample can be measured.

16 Claims, 14 Drawing Sheets

(51) Int. Cl.
  *G01N 23/2273* (2018.01)
  *H01J 49/46* (2006.01)
(58) Field of Classification Search
  USPC .................................... 250/305, 396 R, 397
  See application file for complete search history.

(56) References Cited

U.S. PATENT DOCUMENTS

2016/0047760 A1\* 2/2016 Ujihara ........... H01L 31/035236
                                                              250/305
2016/0327499 A1\* 11/2016 Kobayashi ......... G01N 23/2273
2018/0053643 A1\* 2/2018 Tachibana .............. G01N 27/62

FOREIGN PATENT DOCUMENTS

| JP | H04-343054 A | 11/1992 |
| JP | H09-318437 A | 12/1997 |
| JP | H11-162398 A | 6/1999 |
| WO | 2014/104022 A1 | 7/2014 |

OTHER PUBLICATIONS

May 8, 2018 International Preliminary Report on Patentability issued in Patent Application No. PCT/JP2016/082700.

\* cited by examiner

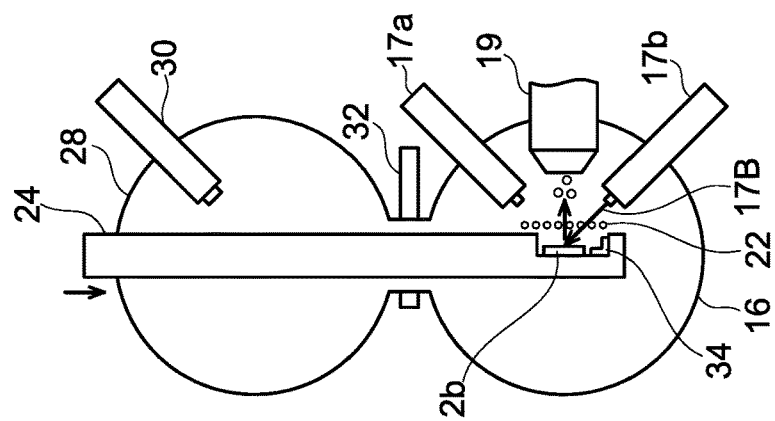
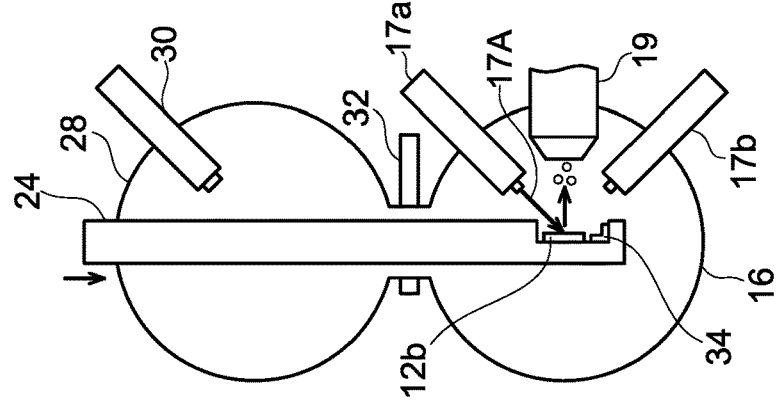
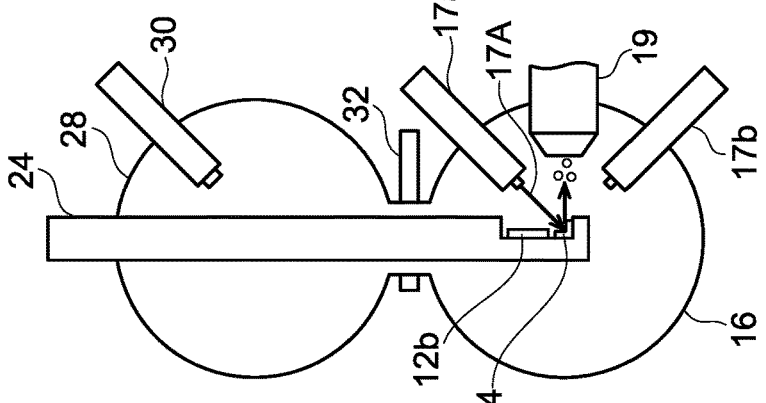
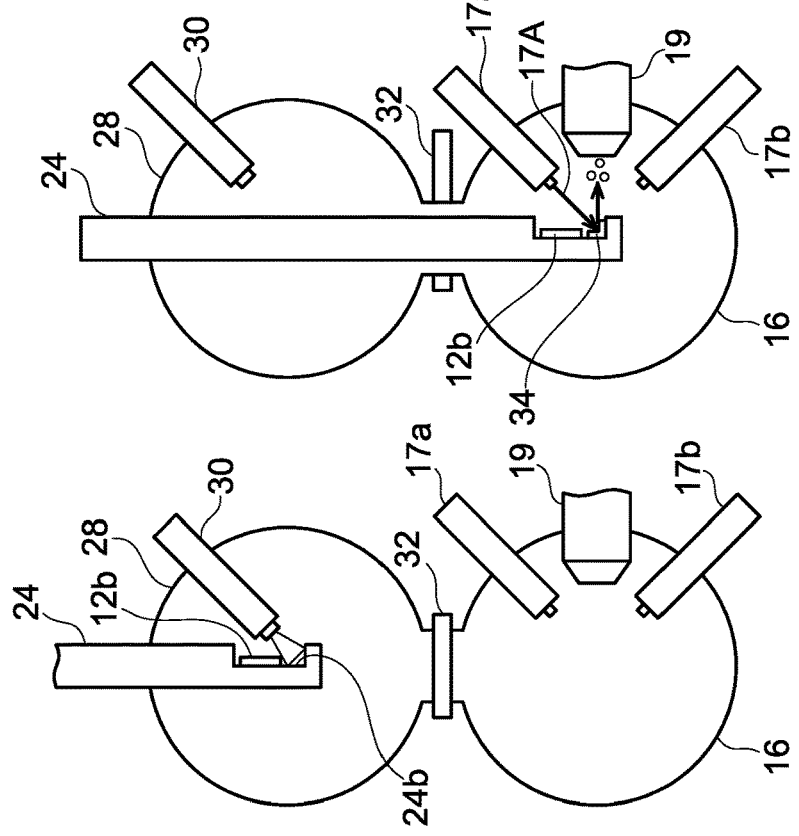

APPARATUS AND METHOD FOR MEASURING ENERGY OF ELECTRONS

TECHNICAL FIELD

The description discloses a technique for measuring energy of electrons excited by a sample being irradiated with a long-wavelength light (such as a visible light and an infrared light) which cannot excite the electrons in the sample to a vacuum level.

BACKGROUND ART

A solar cell supplies power by using electrons that are excited by solar light irradiation on a semiconductor material. In order to improve efficiency of the solar cell, it is useful to know energy of the electrons excited by the solar light. The solar light includes the long-wavelength light that cannot excite the electrons in the semiconductor material to the vacuum level. Other than the solar cell, there are cases where it is useful to measure energy of the electrons excited by irradiating the long-wavelength light that cannot excite the electrons to the vacuum level.

To measure energy of the electrons excited within the sample, it is effective to disperse or split photoelectrons emitted outside the sample from a surface of the sample according to kinetic energy of the photoelectrons. The measurement needs the photoelectrons emitted outside the sample.

Since energy of the electrons excited by the visible light or the infrared light do not reach the vacuum level of the sample in most cases, the photoelectrons are not emitted outside the sample. It makes it difficult to measure energy of the electrons excited by irradiating the visible light or the infrared light.

Thus, a technique of Document I was developed therefor. The technique of Document 1 realizes a state in which a vacuum level of a sample is lower than the lowest energy level of a conduction band (NEA (Negative Electron Affinity)) by processing a surface of the sample. This technique enables measurement of energy of the electrons, which are excited by the visible light or the infrared light, and which would not be emitted outside the sample unless the aforementioned processing is carried out. Electrons having energy not exceeding the vacuum level before the processing are not emitted outside the sample unless the vacuum level of the surface of the sample is lowered.

PRIOR ART DOCUMENT

Patent Document

Document 1: WO 2014/104022 A1

SUMMARY OF INVENTION

Technical Problem

Photoelectrons obtained by irradiating the visible light or the infrared light do not have sufficient kinetic energy, so they remain in a vicinity of the sample surface and create a phenomenon of suppressing new photoelectrons from being emitted (which is called a space charge effect). To provide a countermeasure for the space charge effect, an accelerator for accelerating the photoelectrons emitted from the sample surface toward a photoelectron spectrometer needs to be used. In Document 1, the accelerator is arranged between a vacuum chamber and the photoelectron spectrometer.

The photoelectrons are emitted in various directions from the sample surface. In assuming an angle formed by a normal vector of the sample surface and an emission direction of the photoelectron is termed an emission angle, the emission angle is distributed in a range of 0 to ±90°. The emission angle corresponds to a wavenumber in a direction parallel to the sample surface. The accelerator is effective also for expanding a range of the emission angle that can be subjected to spectroscopy by the photoelectron spectrometer. This is because a large emission angle is adjusted to a small emission angle as a result of acceleration. By being accelerated, an electron beam emitted from the sample is narrowed and the range of the emission angle that can be inputted to the photoelectron spectrometer is enlarged.

In order to provide the countermeasure to the space charge effect using the accelerator and expand the range of the emission angle which can be inputted to the photoelectron spectrometer, it is effective to lessen a distance between the sample and the accelerator. However, when the accelerator is arranged at a position close to the sample and facing the sample, the accelerator interferes with an optical path of the excitation light, and it becomes difficult to irradiate the excitation light to the sample.

In the technique of Document 1, the accelerator is arranged between the vacuum chamber and the photoelectron spectrometer so that the optical path of the excitation light and the accelerator do not interfere. As a result, a distance between the sample and the accelerator becomes long, leaving dissatisfactions regarding countermeasures for the space charge effect and effect of enlarging the range of the emission angle that can be inputted to the photoelectron spectrometer.

Document 1 presents a concept of arranging a conductive mesh at a position facing the sample. This conductive mesh is for preventing a sample holder from affecting photoelectron trajectories, and a voltage that cancels an influence of the sample holder is applied to the conductive mesh. The conductive mesh is not for accelerating the photoelectrons toward the photoelectron spectrometer, and the photoelectrons are accelerated by an accelerator that is separately provided. Further in Document 1, a relationship between the conductive mesh and the optical path of the excitation light is not clear.

The description herein discloses a measuring apparatus that arranges an accelerator in a vicinity of a sample while avoiding an interference with an optical path of an excitation light.

Solution to Technical Problem

A measuring apparatus disclosed herein is an apparatus configured to measure energy of photoelectrons, and comprises: a sample holder configured to hold a sample; a vacuum chamber configured to vacuum a surrounding of the sample held on the sample holder; a excitation light irradiator configured to irradiate the excitation light to the sample held on the sample holder; a photoelectron spectrometer; and an accelerator configured to accelerate photoelectrons emitted from the sample toward the photoelectron spectrometer. The accelerator allows the excitation light and the photoelectrons to pass therethrough.

According to the above, the accelerator can be arranged in a vicinity of the sample while avoiding interference with the optical path of the excitation light. The measuring apparatus leaves no dissatisfactions regarding countermeasures for the space charge effect and effect of enlarging the range of emission angle that can be inputted to the photoelectron spectrometer.

To allow the excitation light and the photoelectrons to pass through, an acceleration electrode including an opening may be used. The excitation light passes via the opening, and the photoelectrons can move via the opening.

When the accelerator comprises the acceleration electrode having the opening, the acceleration electrode can be arranged at a position facing the sample; as a result, energy of the photoelectrons can be measured by irradiating the excitation light to the sample via the opening of the acceleration electrode, attracting the photoelectrons emitted from the sample toward the acceleration electrode using a potential of the acceleration electrode, and sending the photoelectrons emitted from the sample toward the photoelectron spectrometer via the opening of the acceleration electrode.

Energy of the electrons can be measured by using a Fermi level as a reference, that is, a difference between the energy level of the electrons and the Fermi level is measured by the photoelectron spectrometer. In a case where the sample is a semiconductor, the highest energy level of a valence band is preferably used as the energy reference, that is, one want to know a difference between the energy level of the electrons and the highest energy level of the valence band. In order to do so, an energy difference between the Fermi level and the highest energy level of the valence band of the semiconductor needs to be measured.

When a light source configured to irradiate the excitation light with a short wavelength (which is herein called reference excitation light) that can cause excitation to the level higher than the vacuum level is added in addition to the light source configured to irradiate the excitation light with the long wavelength that cannot cause excitation to the vacuum level, a conversion value needed for changing energy measurement references can thereby be specified. In the description herein, in cases where a confusion between the excitation light with the long wavelength and the reference excitation light with the short wavelength needs to be avoided, the former excitation light will be termed primary excitation light. In cases where no confusion will occur with the reference excitation light, the primary excitation light is simply termed the excitation light.

A part of the acceleration electrode having the opening may be irradiated with the primary excitation light upon irradiating the primary excitation light to the sample. However, since electrons in the acceleration electrode will not be excited to the vacuum level by the primary excitation light, photoelectron emission from the acceleration electrode does not occur. That is, the photoelectrons to be measured are endured of being derived from the sample. Co-use of the primary excitation light and the acceleration electrode will not cause any undesirable problem. The energy of the electrons excited by the primary excitation light can be measured while avoiding a space charge effect by using the acceleration electrode.

On the other hand, when the reference excitation light is irradiated to the acceleration electrode, the electrons may be excited to a level higher than the vacuum level. Co-use of the reference excitation light and the acceleration electrode induces photoelectron emission not only from the sample but also from the acceleration electrode, thus measurement of purely sample-derived photoelectrons becomes impossible. The photoelectrons emitted from the sample by the reference excitation light has relatively high energy, and thus do not generate the space charge effect in most cases. Due to this, the acceleration electrode is not necessary in the case of using the reference excitation light.

Thus, the acceleration electrode is preferably configured capable of moving between a facing position facing the sample and a retracted position not facing the sample, and is preferably used in a relationship in which the acceleration electrode is at the facing position when the sample is irradiated with the primary excitation light and the accelerator is at the retracted position when the sample is irradiated with the reference excitation light.

It is preferable that the primary excitation light has a wavelength longer than a wavelength which excites the electrons within the sample to the vacuum level, and the reference excitation light has a wavelength shorter than the wavelength which excites the electrons within the sample to the vacuum level.

By using the primary excitation light, the energy of the electrons excited by the long wave-length light, such as the visible light and the infrared light, can be measured. The photoelectrons derived from the electrons excited by the low energy can be obtained by using the surface film that reduces the vacuum level. The space charge effect can be prevented by using the acceleration electrode.

The Fermi level of the sample and the Fermi level of metal having an equipotent potential as the sample are equal. An energy difference between the Fermi level and the highest energy level of the valence band of the sample can be measured by a comparison of the energy of the photoelectrons, which is excited from the Fermi level of the metal having the equipotent potential as the sample by the reference excitation light and the energy of the photoelectrons, which is excited from the highest energy level of the valence band of the sample by the reference excitation light. The energy difference between the energy of the electrons excited by the primary excitation light and the highest energy of the valence band can be measured.

There are cases where it is useful to use the primary excitation light with a longer wavelength than a wavelength which excites electrons within the acceleration electrode to a vacuum level, and to use the reference excitation light with a shorter wavelength than the wavelength which excites the electrons within the acceleration electrode to the vacuum level. In such a case, photoelectrons would be emitted from the acceleration electrode when the reference excitation light is irradiated through the acceleration electrode, and the measurement might be carried out while including such unintended photoelectrons. It is useful to put aside the acceleration electrode to the retracted position.

It is preferable to use the visible light as the primary excitation light and the ultraviolet light as the reference excitation light. The measuring apparatus can be configured by using general-purpose light sources.

A mesh electrode may be used as the acceleration electrode. However, the acceleration electrode is not limited to the mesh electrode, and it simply needs to be an electrode provided with an opening, such as a ring-shaped electrode.

It is preferable that $D/L<0.1$ is satisfied, where a distance between the sample and the mesh electrode is L and a mesh size of the mesh electrode is D. When the above relationship is satisfied, an electric field in which equipotent potential lines are distributed at equal intervals between the sample and the mesh electrode is obtained, and trajectory calculation of the electrons accelerated by the mesh electrode becomes simplified.

In the actual measurement, the apparatus can be used in a relationship in which the acceleration electrode, the vacuum chamber, and the photoelectron spectrometer are at an equipotent potential and the sample has a negative potential with respect to the aforementioned potential.

In this case, the photoelectrons emitted from the sample are attracted toward the acceleration electrode, and the space charge effect can be prevented from becoming an issue. In the course of the attraction toward the acceleration electrode, a size of the emission angle converges, as a result of which inputting the photoelectrons to the photoelectron spectrometer at emission angles, which would not be inputted to the photoelectron spectrometer unless the convergence takes place, can be achieved. The acceleration electrode functions as an attracting device which prevents the space charge effect, and also functions as a focusing lens for converging photoelectron emission fluxes. When the acceleration electrode, the vacuum chamber, and the photoelectron spectrometer are at the equipotent potential, an electron trajectory between the acceleration electrode and the photoelectron spectrometer becomes linear, and the electron trajectory calculation can be simplified.

A potential difference may be applied between the acceleration electrode and the photoelectron spectrometer. Due to this, the electron trajectory between the acceleration electrode and the photoelectron spectrometer can be adjusted non-linearly.

The sample and the photoelectron spectrometer may have a negative potential with respect to the acceleration electrode. In this case, the electrons traveling from the sample to the acceleration electrode are accelerated and converged. The electrons traveling from the acceleration electrode to the photoelectron spectrometer are decelerated and dispersed. Since the dispersed photoelectron fluxes are inputted to the photoelectron spectrometer, angular resolution related to the emission angle can be refined.

A primary excitation light source and a concave reflector may be arranged outside the vacuum chamber, and the excitation light from the primary excitation light source may be guided into the vacuum chamber by the concave reflector and a window provided on a wall of the vacuum chamber. In this case, a convergence position of the excitation light does not change even when the wavelength of the excitation light is changed. Measurements carried out while changing the wavelength of the excitation light can be simplified. In a case of concurrently introducing two or more types of excitation light, convergence positions of the two or more types of excitation light with different wavelengths can be set at a same position.

A surface film forming chamber configured to form a surface film for reducing the vacuum level to the surface of the sample may be added. The surface film with a constant characteristic can be used in the measurement.

In a case of forming a metal film at a part of the sample surface or at a part of the sample holder and subjecting photoelectrons from the metal film to spectroscopy, a metal film forming chamber configured to form the metal film on the sample surface or on the sample holder may be added.

The description herein further discloses a method of measuring an energy difference between the Fermi level of the sample and the highest energy level of the valence band of the sample. This method comprises irradiating the reference excitation light to the metal film having a same potential as the sample and measuring energy of the photoelectrons emitted from the metal film relative the Fermi level; and irradiating the reference excitation light to the sample having the same potential as the metal film and measuring energy of the photoelectrons emitted from the sample relative to the Fermi level; and measuring the energy difference between the Fermi level and the highest energy level of the valence band of the sample from a difference between the measured energy.

Effects of Invention

According to the measurement technique disclosed in the description herein, a suppressing effect of the space charge effect is increased, and the convergence effect of the photoelectron fluxes emitted from the sample is increased. Energy of photoelectrons with small kinetic energy, with which the space charge effect tends to be problematic, can be measured. Further, the photoelectrons existing in the range of emission angle that would not be inputted to the photoelectron spectrometer unless the convergence takes place can be inputted to the photoelectron spectrometer, and a wide range of the emission angle (corresponding to having a wide wavenumber range) can be measured at once.

BRIEF DESCRIPTION OF DRAWINGS

FIGS. 4A to 4D show a case of measuring a metal film with the ultraviolet light, a case of measuring a sample with the ultraviolet light, and a case of measuring the sample with the visible light.

DESCRIPTION OF EMBODIMENTS

Hereinbelow, some of technical features of embodiments disclosed in the description herein will be listed. Each of the matters listed below has technical usefulness individually.
(Feature 1) A structure of a conduction band of a solar cell is measured.
(Feature 2) A structure of a conduction band of a semiconductor is measured.
(Feature 3) A structure of a superconductor in an unoccupied state is measured.
(Feature 4) A structure of a graphene in an unoccupied state is measured.

(Feature 5) A structure of a conductive oxide (such as InGaZnO) in an unoccupied state is measured.

Embodiments

Figure 1:
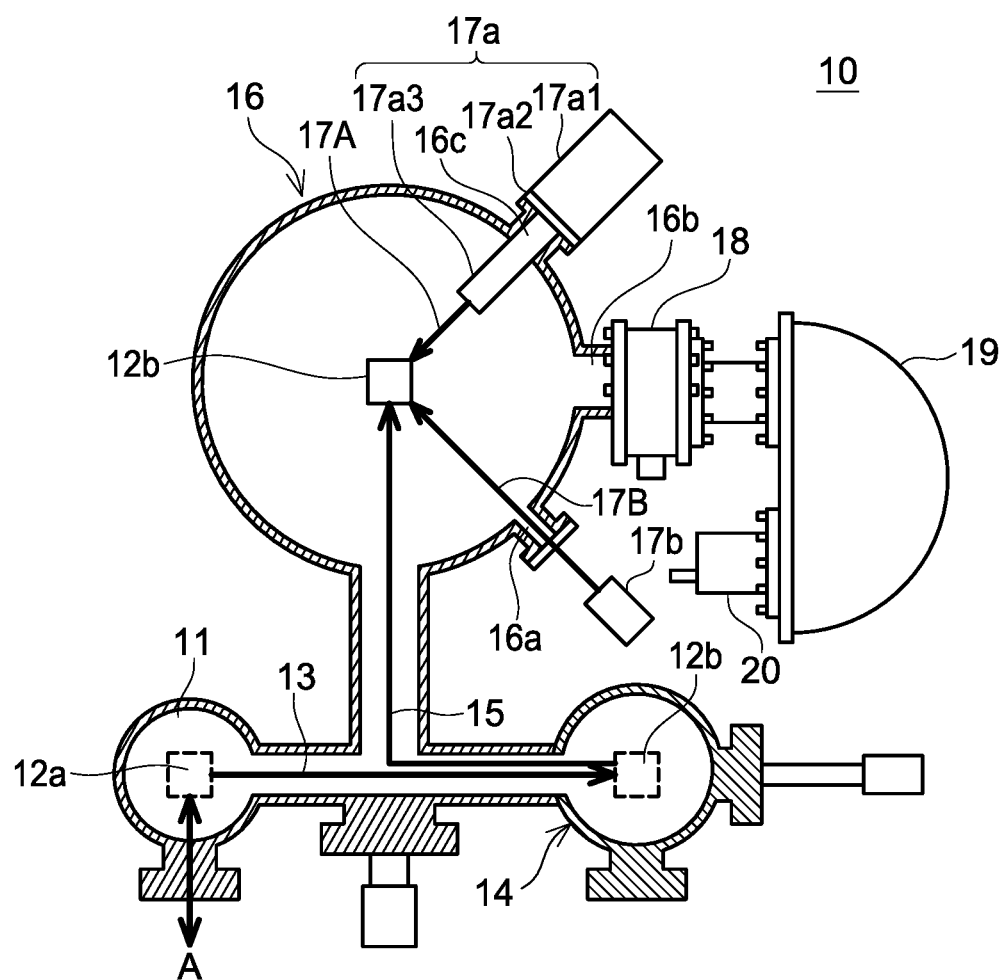
FIG. 1 explains an overall configuration of a measuring apparatus.

FIG. 1 shows an overall configuration of a measuring apparatus 10. Reference sign 11 is a chamber for inputting a sample 12 into the measuring apparatus 10 and taking it out therefrom. An NEA surface is not yet formed on a surface of the sample 12 to be inputted to the measuring apparatus 10. A sample on which the NEA surface is not formed yet will be indicated by reference sign 12a.

The sample 12a inputted to the measuring apparatus 10 passes through a path 13 and is conveyed to an NEA surface forming chamber 14. The NEA surface forming chamber 14 serves as both a heating device and a deposition device. When the sample 12a is conveyed to the NEA surface forming chamber 14, the sample 12a is heated and held for a predetermined time period. A natural oxide film that was formed on the surface of the sample 12a is removed by this heat treatment. A temperature required to remove the natural oxide film depends on types of samples. For example, the sample is heated to 450° C. when the sample is GaAs, and it is heated to 1000° C. when it is Si. Next, the deposition device is actuated. The deposition device is configured of a cesium discharging device that discharges cesium Cs in the chamber 14 and a device for introducing oxygen into the chamber 14. In the cesium discharging device, $CsCrO_4$, a reducer and a getter agent are capsulated in a nichrome sleeve, for example, and the device discharges the cesium Cs vapor by reducing $CsCrO_4$. $CsCrO_4$ is reduced when the nichrome sleeve is heated by applying electric power. The discharged cesium Cs vapor is deposited on the surface of the sample 12a. Then, the oxygen is introduced. The aforementioned two steps are repeated in pair. In so doing, the cesium Cs and the oxygen O are alternately added to the surface of the sample 12a, as a result of which an electric double layer potential having a thickness of substantially a few atom layers is formed, and a vacuum level of the sample surface is reduced. That is, the surface layer from which electrons excited to a conduction band are emitted to vacuum is thereby achieved. The vacuum level of the sample surface lowered by the NEA surface is lower than the highest energy level of a valence band of the sample.

Electrons excited to an intermediate band, which is formed within a bandgap between the highest energy level of the valence band and the lowest energy level of the conduction band, are emitted to the vacuum. A sample on which the NEA surface is formed will be indicated by reference sign 12b. The sample is changed from 12a to 12b in the chamber 14.

The vacuum level obtained by the NEA surface changes sensitive to a forming condition of the NEA surface. To stabilize the vacuum level obtained by the NEA surface, the present embodiment controls formation process of the NEA surface while measuring a photoelectron amount discharged from the surface of the sample 12. By using the measured photoelectron amount as an index, an electric power applied to the heater for reducing $CsCrO_4$ is feedback-controlled. By employing the feedback control, the vacuum level obtained by the NEA surface is stabilized. A YO-YO method is suitable for forming the NEA surface.

A same effect can be achieved by providing a device configured to introduce nitrogen fluoride such as nitrogen trifluoride $NF_3$ instead of introducing oxygen $O_2$ and alternately supply cesium Cs and the nitrogen fluoride to the sample surface.

In some cases, electrons may be excited by visible light to a level higher than the lowest energy level of the conduction band. In such cases, the photoelectrons can be discharged into vacuum without having to lower the vacuum level below the lowest energy level of the conduction band. A film to be formed on the sample surface does not necessarily need to have a negative electron affinity, and it simply needs to be able to lower the vacuum level to a level lower than the energy of the excited electrons. In the description herein, a film formed on the sample surface for lowering the vacuum level is termed an NEA surface, however, it does not necessarily need to have the negative electron affinity. Those capable of lowering the vacuum level of the surface are collectively termed NEA surface.

The semiconductor material 12b on which the NEA surface is formed is conveyed to an excited electron energy measuring chamber 16 through a path 15. Chambers 11, 14, 16 and their paths are in a vacuum environment. Reference sign 17A is vacuum ultraviolet light that irradiates the surface of the sample 12b and a surface of a metal film to be described later. Reference sign 16c is a window provided in a wall of the chamber 16, and is closed by a plate that is transparent to the vacuum ultraviolet light (such as an $MgF_2$ plate) 17a2. A vacuum ultraviolet light generator 17a1 is arranged on an outer side of the transparent plate 17a2, and a monochromator 17a3 is arranged on an inner side of the transparent plate 17a2. The ultraviolet light generator 17a1 is configured to generate the vacuum ultraviolet light {Xe Iα: wavelength 147 nm (excitation energy 8.437 eV)}. The sample 12b is exposed to the vacuum ultraviolet light via the monochromator 17a3. In the description herein, the vacuum ultraviolet light generator 17a1, the transparent plate 17a2, and the monochromator 17a3 are collectively termed an ultraviolet light source 17a. Ultraviolet light may be used as reference excitation light instead of the vacuum ultraviolet light. It may be any light, so long as it is capable of exciting electrons of a metal film and the sample to a level higher than the vacuum level of the metal film and the sample. An ultraviolet laser, a mercury lamp, a helium lamp and the like may be used as the ultraviolet light source instead of the above configuration.

Reference sign 17B is a primary excitation light that irradiates the surface of the sample 12b, which is in this embodiment the visible light. Reference sign 16a is a window provided in a wall of the chamber 16, and is closed by a transparent plate. A visible light source 17b is arranged on an outer side of the transparent plate, and the sample 12b is exposed to the visible light 17B. Details of the visible light source 17b will be described later. A visible light laser, a pseudo-solar lamp, and the like may be used as the visible light source. Infrared light may be used as the primary excitation light instead of the visible light. The primary excitation light may have a long wavelength by which the electrons in the sample cannot be excited to the vacuum level of the sample 12a. Even the case, since the vacuum level of the sample 12b is lowered by the NEA film, excited electrons by this primary excitation light can be measured. Light with a short wavelength by which the electrons in the sample can be excited to the level higher than the vacuum level may be used as the primary excitation light. Even if the excitation is carried out using the light with the short wavelength, electrons that are only excited to the level lower than the vacuum level are generated. By using the apparatus as above, the energy of such low energy electrons can be measured.

Reference sign 18 is a connection flange connecting the excited electron energy measuring chamber 16 and the photoelectron spectrometer 19, reference sign 20 is a CCD camera that captures a spectral image generated by the photoelectron spectrometer 19, and reference sign 16b is a pipe or a connection flange that communicates the excited electron energy measuring chamber 16 and the photoelectron spectrometer 19.

Figure 2:
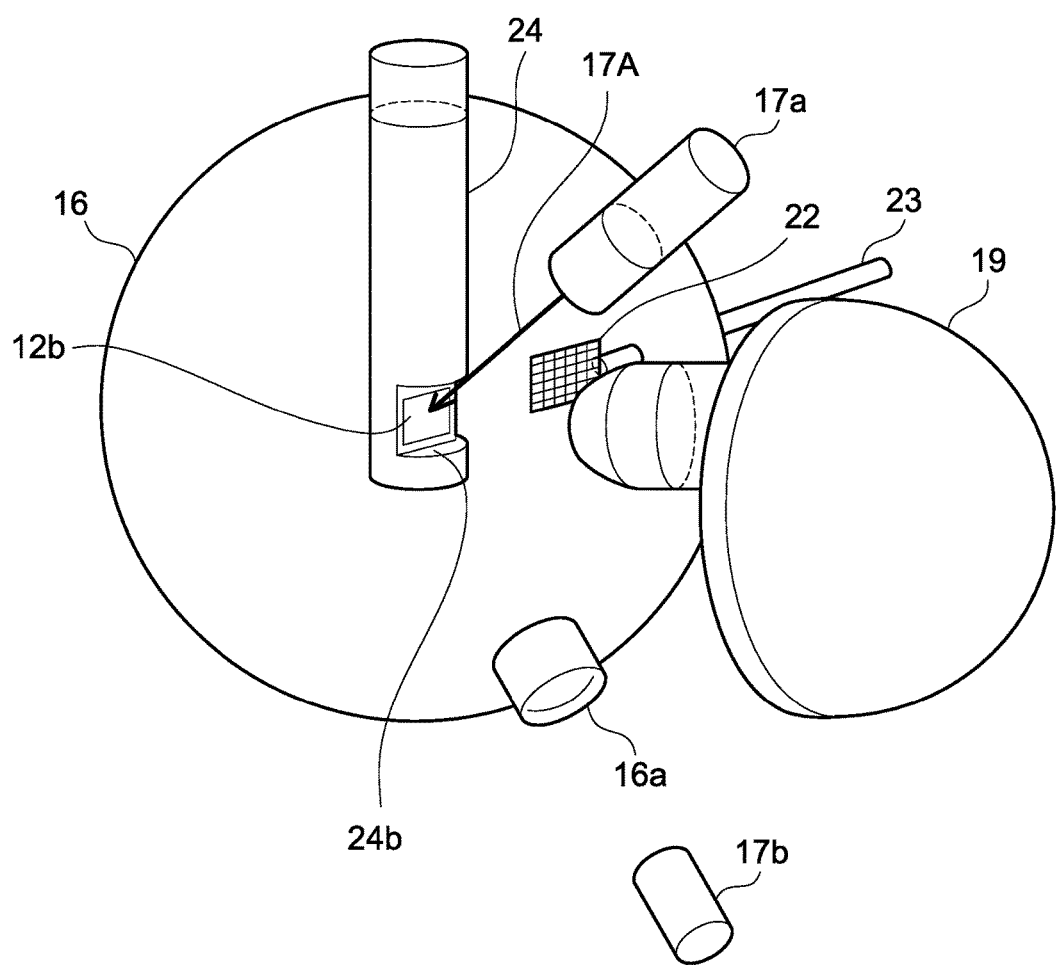
FIG. 2 schematically shows a range directly related to measurement. It illustrates measurement using the ultraviolet light.
Figure 15:
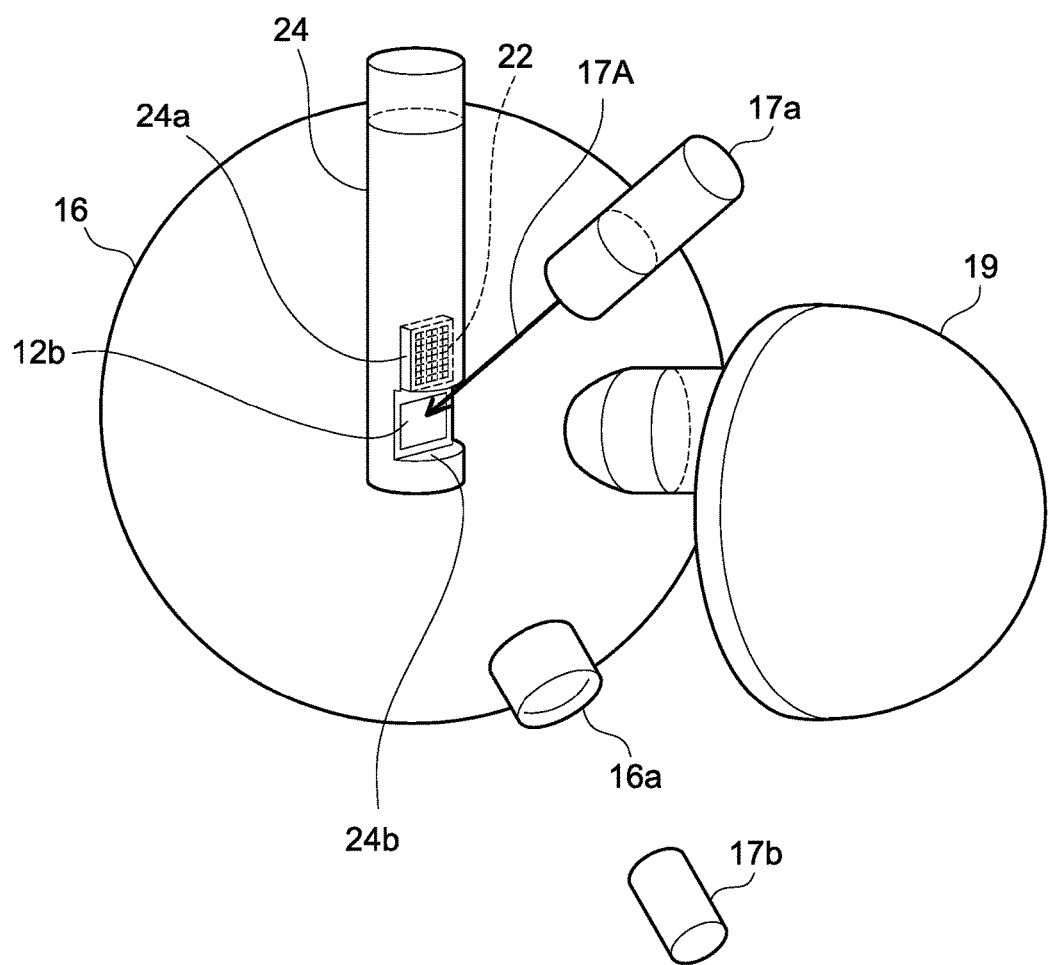
FIG. 15 is a diagram corresponding to FIG. 2 of the second embodiment.
Figure 16:
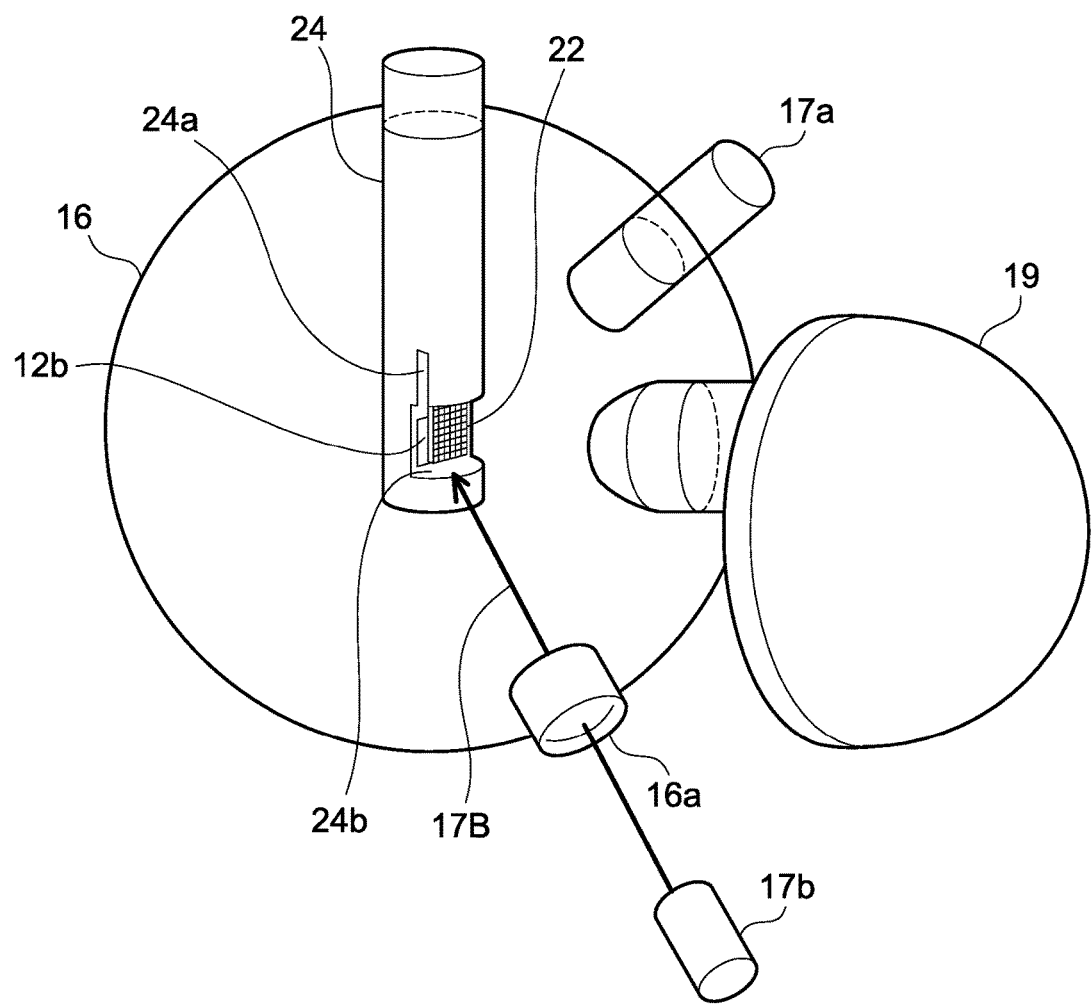
FIG. 16 is a diagram corresponding to FIG. 3 of the second embodiment.

FIG. 2 is a diagram schematically showing an inside of the excited electron energy measuring chamber 16. It shows measurement using the ultraviolet light (reference excitation light) 17A. A mesh electrode 22 to be described later is fixed to a distal end of a rod 23 which can be operated from outside the chamber 16, and a position of the mesh electrode 22 can thereby be changed. A position at which the rod 23 is retracted away from a sample stage 24b is termed a retracted position of the mesh electrode 22. By configuring as above, fine adjustment of a distance between the sample 12b and the mesh electrode 22 can easily be performed. Further, replacement of the mesh electrode 22 also becomes easier. As a configuration of retraction of the mesh electrode 22, as shown in FIGS. 15 and 16, the mesh electrode 22 may be configured to be drawn in and out through a slit 24a provided in a sample holder 24.

In FIG. 2, the ultraviolet light 17A is irradiated to the surface of the sample 12b, and the electrons excited by the ultraviolet light 17A are emitted from the surface of the sample 12b. The photoelectrons discharged by the ultraviolet light have higher energy than the vacuum level, and reach the photoelectron spectrometer 19 without an accelerator to be described later.

The ultraviolet light 17A may be irradiated to the metal film to be described later. An energy difference between the Fermi level and the highest energy level of the valence band of a semiconductor sample can be measured from a spectroscopy result for a case of irradiating the ultraviolet light 17A to the metal film and a spectroscopy result for a case of irradiating the ultraviolet light 17A to the semiconductor sample.

The mesh electrode 22 is retracted in the case of the ultraviolet light 17A irradiation. Unnecessary photoelectrons are prevented from being generated from the mesh electrode 22, and the photoelectrons derived exclusively from the sample or the metal film can accurately be measured. However, the retraction of the mesh electrode may no longer be necessary when a material of the mesh electrode and the wavelength of the ultraviolet light are suitably selected. For example, when the wavelength of 225 nm (5.5 eV) to 234 nm (5.3 eV) is used for the ultraviolet light 17A, platinum (with a work function of 5.6 eV) is used for the mesh electrode 22, and gold (with the work function of 5.2 eV) is used as the metal film, a relationship can be achieved in which photoelectrons are obtained from the metal film (gold) but photoelectrons are not emitted from the mesh electrode (platinum) using the ultraviolet light 17A. In such case, retraction of the mesh electrode is not required.

Figure 3:
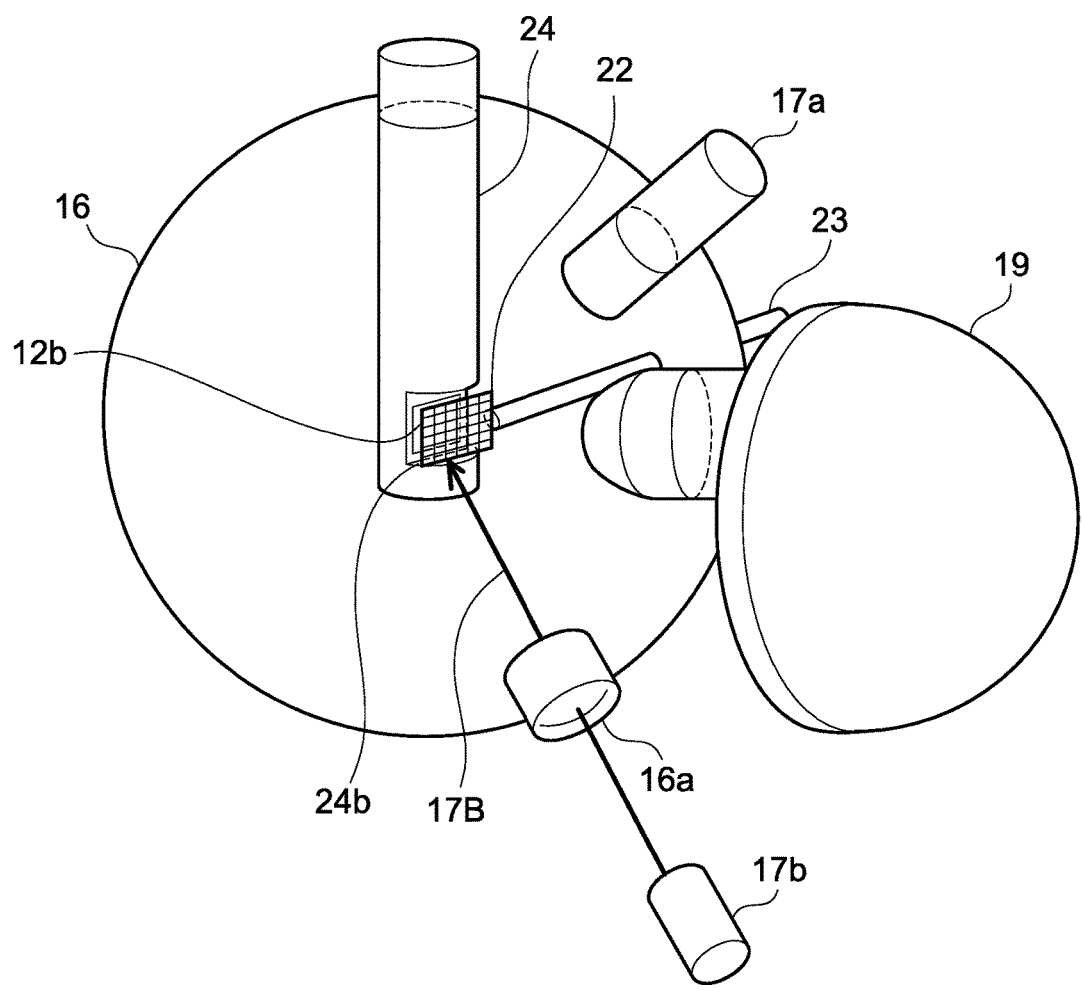
FIG. 3 schematically shows a range directly related to measurement. It illustrates measurement using the visible light.

FIG. 3 shows measurement using the visible light (primary excitation light) 17B. In this case, the mesh electrode 22 is placed at a position facing the surface of the sample 12b. The mesh electrode 22 moves between the retracted position in FIG. 2 and a facing position in FIG. 3 by operation of the rod 23.

Instead of the rod 23, as shown in FIGS. 15 and 16, the slit 24a may be provided in the sample holder 24 so that the mesh electrode 22 is capable of moving between a position where the mesh electrode 22 is accommodated in the slit 24a (FIG. 15) and a position where it is drawn out from the slit 24a (FIG. 16), and the mesh electrode 22 may be moved between the retracted position and the facing position by accommodating a solenoid coil in the sample holder 24.

As shown in FIG. 3, the visible light 17B is irradiated to the mesh electrode 22 and the sample 12b through the mesh electrode 22. A film for lowering the vacuum level is not provided on a surface of the mesh electrode 22. Excited electrons within the mesh electrode 22 are thus not emitted outside the mesh electrode 22. The photoelectrons derived from the electrons exited by the visible light 17B are emitted from the surface of the sample 12a irradiated by the visible light 17B. These photoelectrons have low energy, thus they remain in a vicinity of the sample surface unless a potential is applied to the mesh electrode 22 to strip them off of the sample surface. When the photoelectrons remain at the sample surface, the photoelectrons cannot be subjected to spectroscopy, and a phenomenon in which the emission of the photoelectrons is hindered (space charge effect) may be generated by the remaining photoelectrons. The mesh electrode 22 provides solution to this problem. By applying the potential to the mesh electrode 22, the photoelectrons emitted from the sample surface are accelerated toward the mesh electrode 22, and are attracted from the vicinity of the sample surface. The photoelectrons accelerated by the mesh electrode 22 pass through the mesh electrode 22 and reach the photoelectron spectrometer 19.

FIGS. 4A to 4D show procedures of the measurement. The actual measuring apparatus 10 includes a deposition chamber 28 that is not shown in FIG. 1. A deposition device 30 is arranged in the deposition chamber 28. A recess 24b is provided in the sample holder 24, and the sample 12b is held in the recess 24b. The sample holder 24 on which the sample 12b is held is conveyed to the deposition chamber 28 prior to the actual measurement. In the deposition chamber 28, a metal film is formed by performing vapor deposition processing on a part of the recess 24b. FIG. 4A shows a step of forming the metal film on the sample holder 24, in which the deposition device 30 discharges vapor metal toward the recess 24b and the metal film is formed. The metal film 34 (see FIGS. 4B to 4D), the sample 12b, and the sample holder 24 come to have a same potential. Gold (Au) may be used for example for the metal film 34.

FIG. 4B shows a state in which the metal film 34 is conveyed to the chamber 16, the ultraviolet light 17A (reference excitation light) is irradiated to the metal film 34, and the energy of the photoelectrons emitted from the metal film 34 irradiated with the ultraviolet light 17A is subjected to spectroscopy by the photoelectron spectrometer 19. The mesh electrode 22 is at the retracted position, and is not involved in the measurement.

FIG. 4C shows a state in which the ultraviolet light 17A (reference excitation light) is irradiated to the sample 12b, and the energy of the photoelectrons emitted from the sample 12b irradiated with the ultraviolet light 17A is subjected to spectroscopy by the photoelectron spectrometer 19. The mesh electrode 22 is at the retracted position, and is not involved in the measurement.

FIG. 4D shows a state in which the visible light 17B (primary excitation light) is irradiated to the sample 12b, and the energy of the photoelectrons emitted from the sample 12b irradiated with the visible light 17B is subjected to spectroscopy by the photoelectron spectrometer 19. The mesh electrode 22 is at the facing position. The visible light 17B is irradiated to the sample 12b via the mesh electrode 22. The photoelectrons travel from the sample 12b through the mesh electrode 22 to the photoelectron spectrometer 19.

The photoelectrons are attracted toward the mesh electrode 22 between the sample 12b and the mesh electrode 22, and are thereby accelerated.

Figure 5:
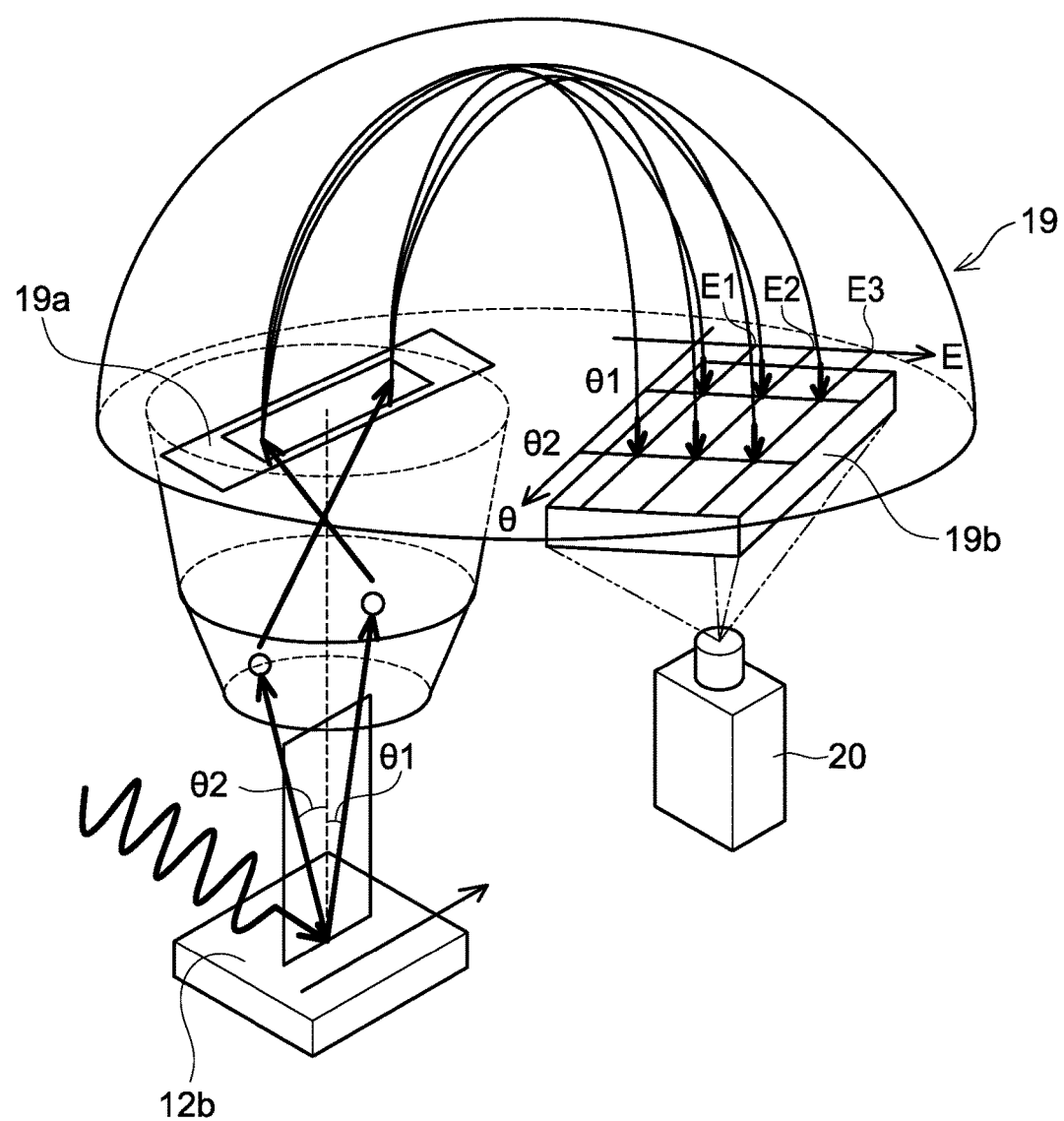
FIG. 5 schematically shows how photoelectron spectrometer performs spectroscopy by energy and wavenumber.

FIG. 5 shows a spectral phenomenon generated by the photoelectron spectrometer 19. The photoelectrons are dispersed or split along an E-axis direction according to magnitudes of their energy. The energy of the photoelectrons can be measured from positions where the photoelectrons have reached in the B-axis direction. Further, the photoelectrons are dispersed or split along a θ-axis direction according to their emission angles from the sample surface (see angles θ1, θ2 relative to a normal vector vertically extending on the sample surface). The emission angles of the photoelectrons (that is, the wavenumber thereof) can be measured from positions where the photoelectrons have reached in the θ-axis direction. The CCD camera 20 records reached positions of the photoelectrons in a two-dimensional surface of an E axis and a θ axis.

Figure 7:
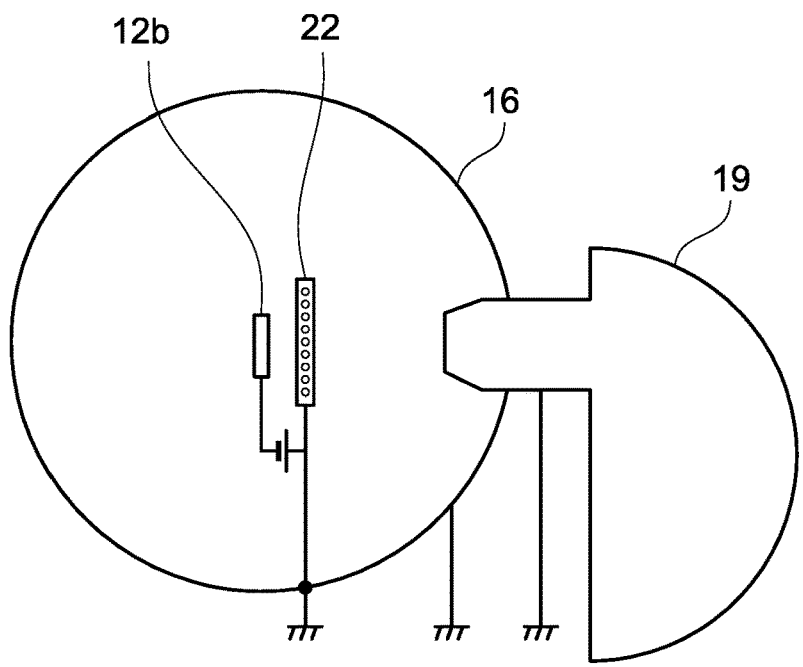
FIG. 7 shows a first embodiment of the accelerator.

FIG. 7 shows a relationship of potentials of the sample 12b, the mesh electrode 22, the chamber 16, and the photoelectron spectrometer 19. In FIG. 7, a negative potential is applied to the sample 12b, and the mesh electrode 22, the chamber 16, and the photoelectron spectrometer 19 are grounded. The potential of the mesh electrode 22 is higher than that of the sample 12b, so the photoelectrons existing in a vicinity of the sample 12b are accelerated toward the mesh electrode 22. The photoelectrons that have passed through the mesh electrode 22 advance straight and enter the photoelectron spectrometer 19. By grounding the mesh electrode 22, the chamber 16, and the photoelectron spectrometer 19, a photoelectron path between the mesh electrode 22 and the photoelectron spectrometer 19 becomes straight, so a calculation process of analyzing the images from the CCD camera 20 to convert to energy and wavenumber can be simplified.

Figure 6:
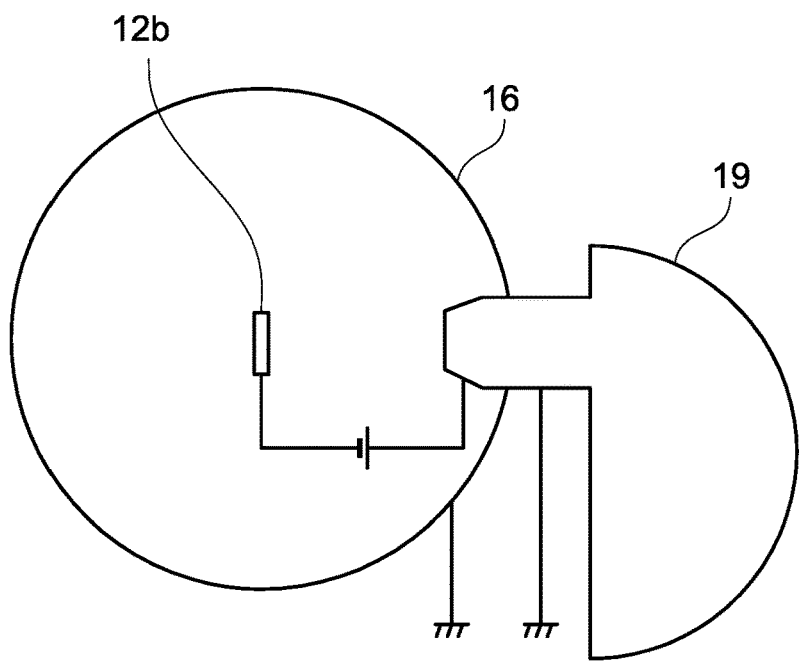
FIG. 6 shows a comparative example of an accelerator.

FIG. 6 shows an embodiment in which a potential difference is applied between a sample and the photoelectron spectrometer 19 to accelerate the photoelectrons toward the photoelectron spectrometer 19. This corresponds substantially to conventional technique.

As it is apparent by comparing FIGS. 6 and 7, in a comparative example of FIG. 6, it is difficult to sufficiently focus the photoelectrons, which were emitted from the sample surface at shallow angles, in the photoelectron spectrometer 19 with the mere bias applied between the sample 12b and the photoelectron spectrometer 19. According to the embodiment of FIG. 7, the mesh electrode 22 is arranged in a vicinity of the sample 12b, so when a bias voltage that is same as FIG. 6 is applied between the sample 12b and the mesh electrode 22, intervals between equipotential planes become dense as compared to FIG. 6, so even the photoelectrons emitted from the sample surface at shallow angles can be focused sufficiently in the photoelectron spectrometer 19.

When the accelerator is arranged in the vicinity of the sample, the accelerator and the excitation light interfere with each other. In the present embodiment, both features of irradiating the sample with the excitation light and arranging the accelerator in the vicinity of the sample can be achieved concurrently by configuring the accelerator to allow the excitation light to pass therethrough.

Figure 8:
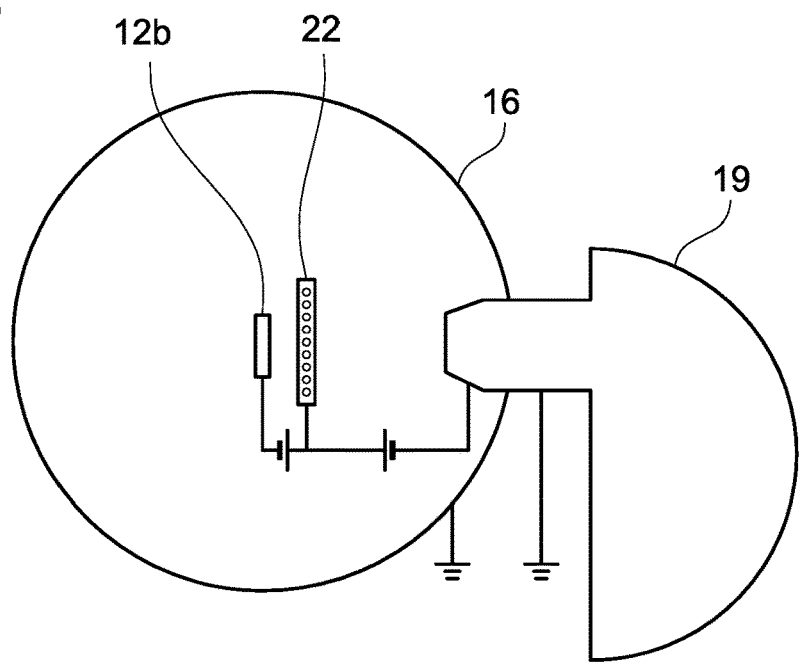
FIG. 8 shows a second embodiment of the accelerator.

FIG. 8 shows a relationship of potentials in a second embodiment. A negative potential is applied to the sample 12b, a positive potential is applied to the mesh electrode 22, and the chamber 16 and the photoelectron spectrometer 19 are grounded. The potential of the mesh electrode 22 is higher than that of the sample 12b, and the photoelectrons existing in the vicinity of the sample 12b are accelerated toward the mesh electrode 22. The photoelectrons that have passed the mesh electrode 22 are decelerated, and enter the photoelectron spectrometer 19. According to the potential application shown in FIG. 8, by setting the bias between the sample 12b and the mesh electrode 22 (for example, setting the sample to 0V and setting the mesh to +10V) to accelerate the photoelectrons, the electrons in a wide angle can be focused to a narrower angle. Further, the electrons emitted from the sample can swiftly be separated away from the sample, so the electrons can be drawn out in a constant manner irrelevant to a measurement environment such as quantum efficiency of the sample and an excitation light intensity. Further, by setting the bias between the mesh electrode 22 and the photoelectron spectrometer 19 (for example, setting the mesh to +10V and setting the photoelectron spectrometer to 0V) to decelerate the photoelectrons, the photoelectrons focused to the narrow angle can be recovered to a wide angle, and an angular resolution can be increased.

Figure 9:
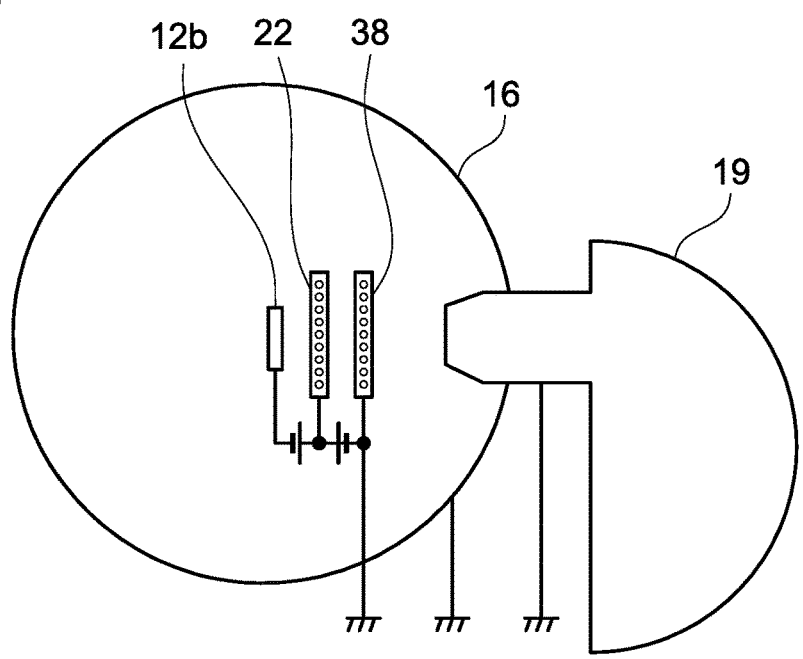
FIG. 9 shows a third embodiment of the accelerator.

FIG. 9 shows a relationship of potentials in a third embodiment. In this embodiment, a second mesh electrode 38 is added immediately in front of the photoelectron spectrometer 19. The chamber 16, the photoelectron spectrometer 19, and the mesh electrode 38 are grounded, the mesh electrode 22 is given a positive potential, and the sample is given a ground potential or a negative potential. In this case, the photoelectrons in the vicinity of the sample are accelerated toward the mesh electrode 22 and are converged. The photoelectrons that have passed the mesh electrode 22 are decelerated by a potential difference between the mesh electrode 22 and the second mesh electrode 38, and are dispersed. The photoelectrons that have passed the second mesh electrode 38 advance straight without being accelerated or decelerated and enter the photoelectron spectrometer 19. According to this embodiment, all of no electron buildup in the vicinity of the sample surface, refinement of the measurable angular resolution, and simplification of the calculation process of converting to energy and wavenumber by simplification of the photoelectron path can be achieved.

Figure 10A:
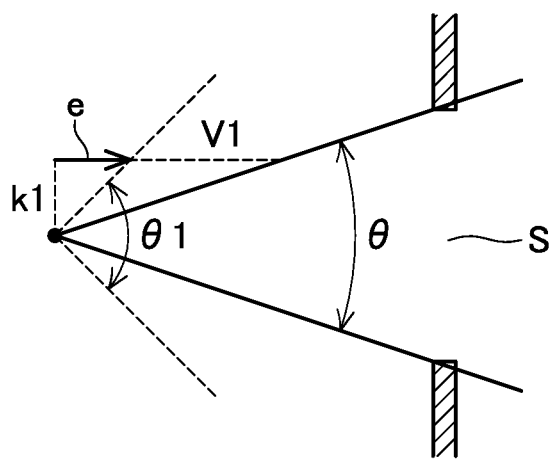
FIGS. 10A and 10B schematically show a relationship of acceleration and a measurable wavenumber range.
Figure 10B:
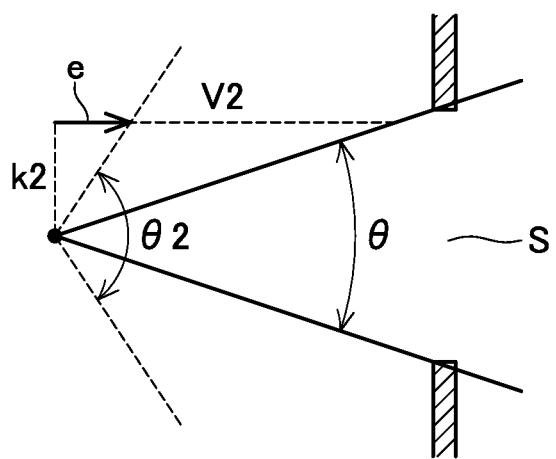

FIGS. 10A and 10B schematically show that the range of the emission angle inputted to the photoelectron spectrometer (wavenumber range) is enlarged by accelerating the photoelectrons from the sample toward the photoelectron spectrometer.

In FIGS. 10A and 10B, S indicates an incident slit of the photoelectron spectrometer 19, and the photoelectrons that have passed through this slit are subjected to spectroscopy. Further, broken lines indicate the emission angle of the photoelectrons in a case of no acceleration. e in these drawings indicates a speed component by which the unaccelerated photoelectrons travel from the sample toward the photoelectron spectrometer 19, and is identical between 10A and 10B.

FIG. 10A shows a case where an acceleration voltage is small, and the speed component increases by V1 by accelerating the photoelectrons toward the photoelectron spectrometer. FIG. 10B shows a case where the acceleration voltage is large, and the speed component increases by V2 by accelerating the photoelectrons toward the photoelectron spectrometer. As it is apparent by comparing FIGS. 10A and 10B, only the photoelectrons having the wavenumber equal to or less than k1 enter the slit S in the case of FIG. 10A, whereas in the case of FIG. 10B, the photoelectrons having the wavenumber equal to or less than k2 enter the slit S. Here, k1<k2 is satisfied. That is, in the case where the acceleration voltage is small, only the photoelectrons having the wavenumber equal to or less than k1 and discharged within the emission angle equal to or less than θ1 can be subjected to spectroscopy by the photoelectron spectrometer, whereas in the case where the acceleration voltage is large, the photoelectrons having the wavenumber equal to or less than k2 and discharged within the emission angle equal to or less than θ2 can be subjected to spectroscopy by the photoelectron spectrometer. θ1<θ2 is satisfied. It can be understood that more intense acceleration enables the range of the emission angle capable of being subjected to spectroscopy to become wider.

In the cases of FIGS. 7 to 9, the acceleration electrode 22 is arranged close to the sample, and the intervals of the equipotential lines are dense between the sample and the acceleration electrode 22. The photoelectrons are accelerated intensively toward the acceleration electrode. In the present embodiments, the range of the emission angle inputted to the photoelectron spectrometer can be widened to substantially±90°.

Figure 11A:
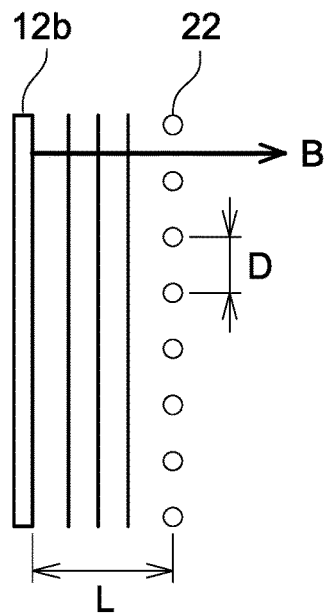
FIGS. 11A and 11B schematically show an influence of a mesh size.
Figure 11B:
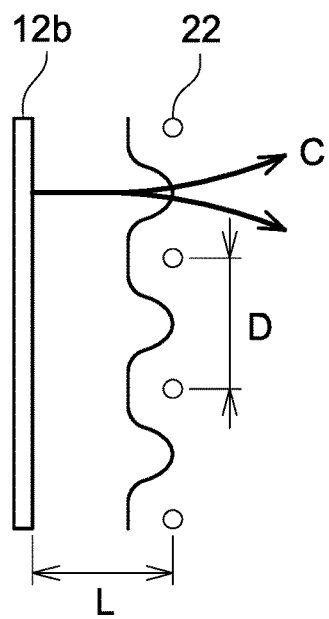

FIGS. 11A and 11B show a relationship between an interval L between the sample 12b and the mesh electrode 22 and a mesh size D. FIG. 11A shows a case of "D/L<0.1", and since an electric field in the vicinity of the mesh electrode 22 does not curve, the photoelectrons accelerated from the vicinity of the sample 12b toward the mesh electrode 22 pass through the mesh electrode without receiving lens effect. FIG. 11B shows a case of "D/L>0.1", where an effect by which the electric field in the vicinity of the mesh electrode 22 curves becomes prominent and the photoelectrons receive the lens effect. It is preferable to use the mesh electrode satisfying "D/L<0.1".

Here, when L is set excessively large, the voltage applied between the sample 12b and the mesh electrode 22 needs to be enlarged, and the electric field in the vicinity of the sample 12b becomes susceptible to external influences. On the other hand, when L is set excessively small, D needs to be made smaller, causing interference between the visible light to be irradiated to the sample and the mesh electrode, and a problem occurs in which an optical amount of the visible light reaching the sample is reduced. In the present embodiments, a distance between the sample and an inlet port of the photoelectron spectrometer is set to 35 mm and L is set to 3 mm. Further, D is set to about 100 μm. When L is about 3 mm, a potential distribution between the sample and the mesh electrode is determined according to the potential of the mesh electrode, and is not affected by the external influences. The mesh electrode not only widens the range of the emission angle that can be subjected to spectroscopy, but also prevent external disturbances from affecting measurement accuracy.

Figure 12:
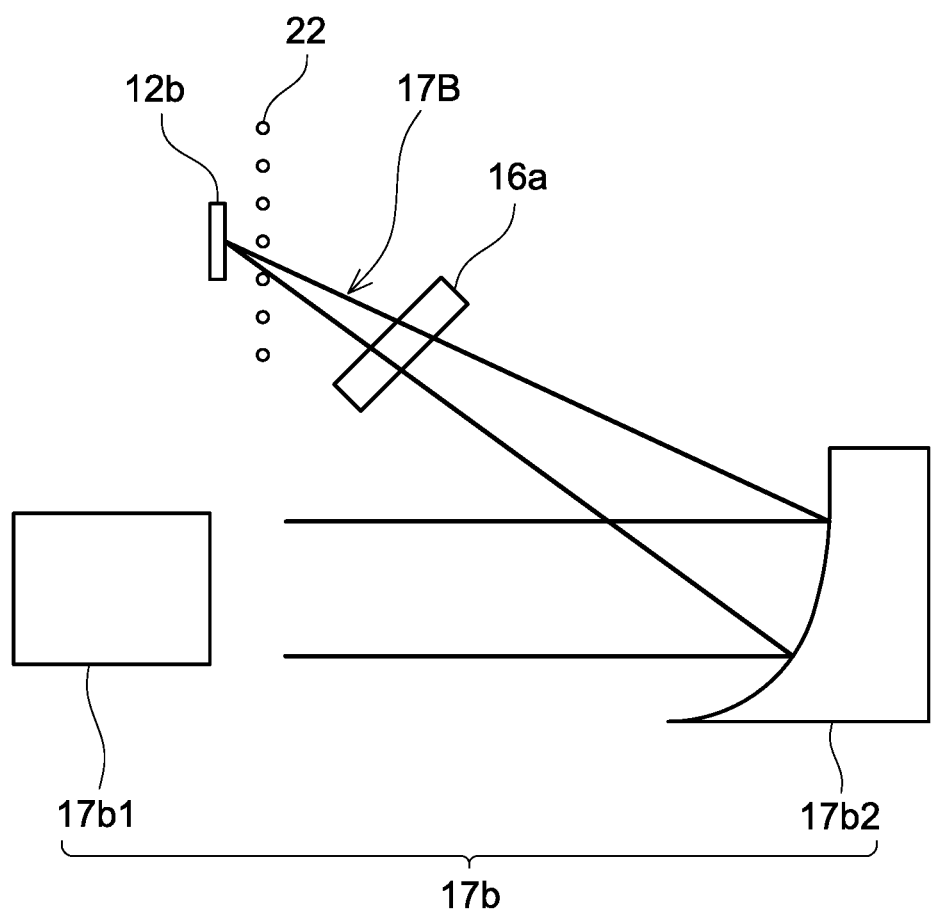
FIG. 12 schematically shows a visible light irradiator.

FIG. 12 shows a relationship between the visible light source 17b, the window 16; the mesh electrode 22, and the sample 12b. The visible light source 17b is arranged outside the chamber 16. The visible light source 17b is configured of a visible light generator 17b1 and a concave reflector 17b2, the visible light 17B from the visible light generator 17b is reflected by the concave reflector 17b2, passes through the window 16a, and focuses on the surface of the sample 12b. The concave reflector 17b2 is also arranged outside the chamber 16. When the light is focused on the surface of the sample 12b by the concave reflector 17b2, a focus is always obtained on the surface of the sample 12b irrelevant to the wavelength of the visible light 17B. A variable wavelength light source may be used as the visible light generator 17b1, and the photoelectron energy can be measured while varying the wavelength. The sample may be irradiated with two types of visible light with different wavelengths.

Figures 13A, 13B:
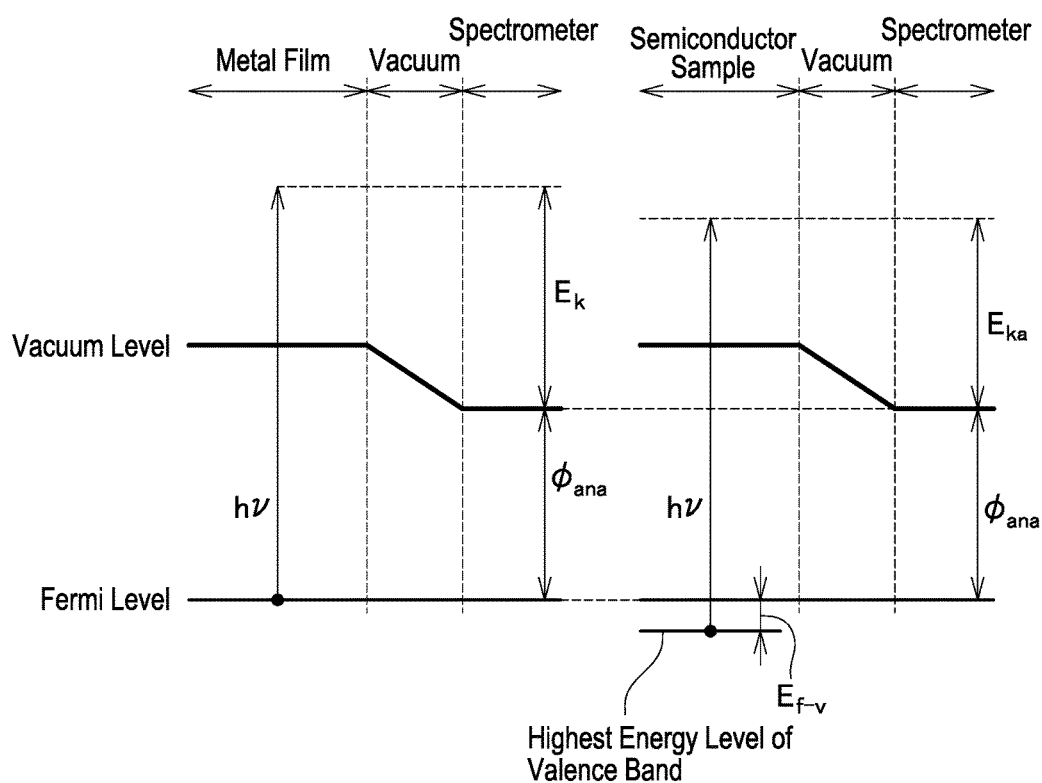
FIGS. 13A and 13B show a relationship of levels during energy measurement of photoelectrons using the ultraviolet light.

FIGS. 13A and 13B show a relationship of the energy levels of the metal film 34 and the semiconductor sample 12b. It shows the case where the metal film 34 and the sample 12b are at the same potential and the ultraviolet light (reference excitation light) 17A is irradiated to each of them. Since the sample 12b and the metal film 34 are at the same potential, their Fermi levels are equal. When the ultraviolet light is irradiated to the metal film 34, the electrons in the metal film are excited from the Fermi level, and rise to an energy state that is higher than the Fermi level by hv. This energy state is higher than the vacuum level, so the photoelectrons are emitted. The photoelectron spectrometer has a unique work function of φana between the Fermi level and the vacuum level, and kinetic energy Ek of the photoelectrons is measured by using the vacuum level as a reference.

FIG. 13B shows a case of irradiating the ultraviolet light 17A with the same wavelength to the semiconductor sample 12b, and the electrons in the sample 12b are excited from the top of the valence band (the highest energy level of the valence band). Ef–v is an energy difference between the Fermi level and the highest energy level of the valence band, and a relationship is satisfied in which the energy of the excited electrons in the sample 12b is lower than the energy of the excited electrons in the metal film 34 by Ef–v. Energy Eka of the photoelectrons (photoelectrons from the sample 12b) measured by the photoelectron spectrometer is in a relationship of being lower than energy Ek of the photoelectrons (photoelectrons from the metal film 34) measured by the photoelectron spectrometer by Ef–v. That is, a relationship of Ek–Eka=Ef–v is satisfied, and Ef–v can be found from measured values of Ek and Eka.

Figure 14:
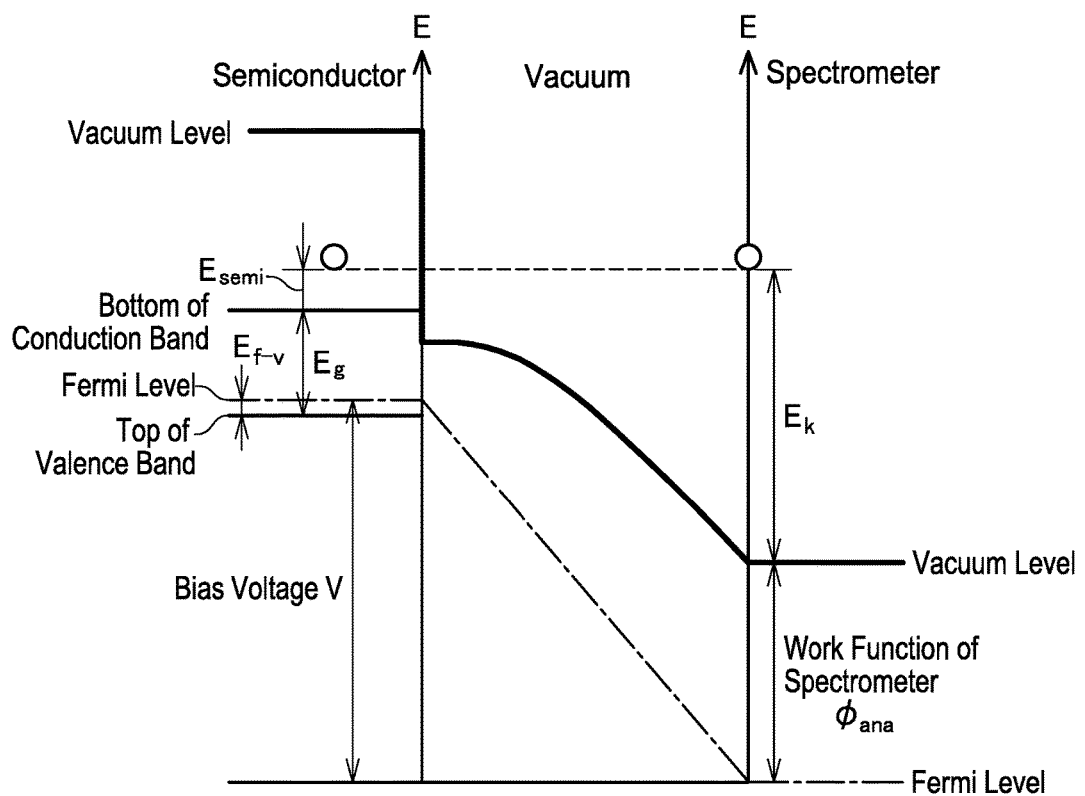
FIG. 14 shows a relationship of the levels during energy measurement of the photoelectrons using the visible light.

FIG. 14 shows a relationship of the energy level in a case where the visible light (primary excitation light) is irradiated to the sample 12b on which the NEA surface is formed. The Fermi level of the sample 12b and the Fermi level of the photoelectron spectrometer differ by a bias voltage V applied to the accelerator for accelerating the photoelectrons from the sample toward the photoelectron spectrometer. When the visible light is irradiated to the sample 12b, the electrons in the sample are exited from the highest energy level of the valence band. The energy of these excited electrons is lower than the vacuum level of the semiconductor, however, since the NEA surface is provided, a relationship of "energy level of excited electrons>vacuum level at the sample surface" is satisfied, so the photoelectrons are emitted from the sample surface and the value of Ek is measured by the photoelectron spectrometer.

What actually is aimed to know is the difference between the highest energy level of the valence band and the energy level of excited electrons, and this value (that is, a value of Eg+Esemi) can be obtained from an equation of V−Ef−v+Eg+Esemi=φana+Ek. That is, from the measured value Ek, the energy Eg+Esemi of the excited electrons relative to the highest energy level of the valence band as the reference can be obtained. If a bandgap Eg of the sample 12b is known, the energy Esemi of the excited electrons relative to the lowest energy level of the conduction band as the reference can also be obtained.

The Fermi level of the sample changes according to a temperature. Ek of FIG. 14 and Ef–v of FIG. 13B need to be measured at a same temperature. Thus, in the present embodiments, the metal film 34 is formed at a part of the surface of the sample 12b. Then, the ultraviolet light is used to measure the energy difference between the Fenni level and the highest energy level of the valence band, and the visible light is used to measure the value of Ek of FIG. 14. Both measurements can be carried out at the same temperature. According to the present apparatus 10, the energy difference between the energy of the excited electrons and the highest energy level of the valence band can be measured. Alternatively, an energy difference between the energy of the excited electrons and the lowest energy level of the conduction band can be measured.

Walls surrounding the chamber 16 are preferably formed by a material with high magnetic permeability. Electric fields outside the measuring apparatus 10 can be prevented easier from affecting the spectroscopy results. Further, the distance between the sample 12b and the mesh electrode 22 is preferably short. In the present embodiments, it is set to 3 mm. When the sample 12b and the mesh electrode 22 are close to each other, changes in the electric fields outside the measuring apparatus 10 can easily be prevented from affecting the spectroscopy results. A method of forming the mesh electrode 22 is not particularly limited. The mesh may be formed of string materials, or may be a mesh formed by punching holes in a plate material. It simply needs to enable visible light irradiation to the sample through the mesh and allow the photoelectrons to pass therethrough. Further, instead of the meshed pattern, it may have a slit pattern. Alternatively, it may be a ring electrode.

An irradiation range by the visible light can be adjusted. A wide range of the sample 12b may be irradiated at once. A narrow range in the sample 12b may be irradiated. In the latter case, it may possible to scan the irradiation spot in the surface of the sample 12b.

FIGS. 15 and 16 show other embodiments in which the mesh electrode 22 moves between the retracted position (FIG. 15) and the facing position (FIG. 16), and the sample holder 24 may be provided with the slit 24a for accommodating the mesh electrode 22 and the solenoid coil (not shown) for sliding the mesh electrode.

Specific examples of the present invention have been described in detail, however, these are mere exemplary indications and thus do not limit the scope of the claims. The art described in the claims includes modifications and variations of the specific examples presented above.

Technical features described in the description and the drawings may technically be useful alone or in various combinations, and are not limited to the combinations as originally claimed. Further, the art described in the description and the drawings may concurrently achieve a plurality of aims, and technical significance thereof resides in achieving any one of such aims.

REFERENCE SIGNS LIST

10: Measuring apparatus
11: Chamber for putting in and taking out sample to and from measuring apparatus
12a: Semiconductor sample before NEA surface is formed
12b: Semiconductor sample after NEA surface is formed
13: Vacuum path
14: NEA surface forming chamber
15: Vacuum path
16: Excited electron energy measuring chamber
16a, 16b, 16c: Window
17a: Ultraviolet light source
17a1: Ultraviolet light generator
17a2: Ultraviolet light transparent plate
17a3: Monochromator
17A: Ultraviolet light
17b: Visible light source
17b1: Visible light generator
17b2: Concave reflector
17B: Visible light
18: Connector
19: Photoelectron spectrometer
20: CCD camera
22: Mesh electrode
23: Mesh electrode holder
24: Sample holder
24a: Slit
24b: Recess
28: Deposition chamber
30: Deposition device
34: Metal film (Au film)
38: Second mesh electrode

The invention claimed is:

1. An apparatus configured to measure energy of photoelectrons, the apparatus comprising:
a sample holder configured to hold a sample;
a vacuum chamber configured to vacuum a surrounding of the sample held on the sample holder;
a primary excitation light irradiator configured to irradiate a primary excitation light to the sample held on the sample holder;
a reference excitation light irradiator configured to irradiate a reference excitation light to the sample held on the sample holder;
a photoelectron spectrometer; and
an accelerator configured to accelerate photoelectrons emitted from the sample held on the sample holder toward the photoelectron spectrometer,
wherein the accelerator allows the primary excitation light and the photoelectrons to pass therethrough.

2. The measuring apparatus according to claim 1, wherein the accelerator comprises an acceleration electrode including an opening.

3. The measuring apparatus according to claim 2, wherein the acceleration electrode is a mesh electrode.

4. The measuring apparatus according to claim 3, wherein $D/L<0.1$ is satisfied, where a distance between the sample and the mesh electrode is L and a mesh size of the mesh electrode is D.

5. The measuring apparatus according to claim 2, wherein
the acceleration electrode, the vacuum chamber, and the photoelectron spectrometer have an equipotent potential, and
the sample has a negative potential with respect to the equipotent potential.

6. The measuring apparatus according to claim 2, wherein
a potential difference exists between the sample and the acceleration electrode, and
a potential difference exists between the acceleration electrode and the photoelectron spectrometer.

7. The measuring apparatus according to claim 6, wherein the sample and the photoelectron spectrometer have a negative potential with respect to the acceleration electrode.

8. The measuring apparatus according to claim 1, wherein one of the primary excitation light irradiator and the reference excitation light irradiator is selectively driven.

9. The measuring apparatus according to claim 8, wherein
a wavelength of the reference excitation light is shorter than a wavelength of the primary excitation light,
the accelerator is configured capable of moving between a facing position facing the sample and a retracted position not facing the sample, and
the accelerator is at the facing position when the sample is irradiated with the primary excitation light and the accelerator is at the retracted position when the sample is irradiated with the reference excitation light.

10. The measuring apparatus according to claim 9, wherein
 the wavelength of the primary excitation light is longer than a wavelength which excites electrons within the sample to a vacuum level, and
 the wavelength of the reference excitation light is shorter than the wavelength which excites the electrons within the sample to the vacuum level.

11. The measuring apparatus according to claim 10, wherein
 the primary excitation light is visible light, and
 the reference excitation light is ultraviolet light.

12. The measuring apparatus according to claim 9, wherein
 the wavelength of the primary excitation light is longer than a wavelength which excites electrons within the accelerator to a vacuum level, and
 the wavelength of the reference excitation light is shorter than the wavelength which excites the electrons within the accelerator to the vacuum level.

13. The measuring apparatus according to claim 1, wherein
 a primary excitation light source and a concave reflector are arranged outside the vacuum chamber, and
 the primary excitation light from the primary excitation light source is guided into the vacuum chamber by the concave reflector and a window provided on a wall of the vacuum chamber.

14. The measuring apparatus according to claim 1, further comprising:
 a surface film forming chamber configured to form a surface film on a surface of the sample, the surface film being configured to reduce vacuum level,
 wherein the surface film forming chamber and the vacuum chamber are connected via a path.

15. A method of measuring an energy difference between a Fermi level and a highest energy level of a valence band of a sample, the method comprising:
 irradiating a reference excitation light to a metal having a same potential as the sample and measuring energy of photoelectrons emitted from the metal with respect to the Fermi level;
 irradiating the reference excitation light to the sample and measuring energy of photoelectrons emitted from the sample with respect to the Fermi level; and
 measuring the energy difference between the Fermi level and the highest energy level of the valence band of the sample from a difference between the measured energy.

16. A method of measuring energy of photoelectrons, the method comprising:
 arranging an acceleration electrode including an opening at a position facing a sample;
 irradiating a primary excitation light to the sample via the opening of the acceleration electrode;
 attracting photoelectrons emitted from the sample toward the acceleration electrode using a potential of the acceleration electrode;
 sending the photoelectrons to a photoelectron spectrometer via the opening of the acceleration electrode;
 measuring energy of the photoelectrons by the photoelectron spectrometer relative to a Fermi level; and
 correcting the measured energy relative to the Fermi level based on an energy difference between the Fermi level and the highest energy level of the valence band measured by using the method according to claim 15 to measure energy of the photoelectrons relative to the highest energy level of the valence band or the lowest energy level of a conduction band.

\* \* \* \* \*